United States Patent

Bymaster et al.

[11] Patent Number: 6,034,108
[45] Date of Patent: Mar. 7, 2000

[54] METHOD FOR TREATING MENTAL RETARDATION

[75] Inventors: Franklin P Bymaster, Brownsburg; Harlan E Shannon, Carmel, both of Ind.

[73] Assignee: Eli Lilly and Company, Indianapolis, Ind.

[21] Appl. No.: 09/202,519

[22] PCT Filed: Jul. 28, 1997

[86] PCT No.: PCT/US97/13184

§ 371 Date: Dec. 16, 1998

§ 102(e) Date: Dec. 16, 1998

[87] PCT Pub. No.: WO98/05291

PCT Pub. Date: Feb. 12, 1998

[51] Int. Cl.[7] .................................................. A61K 31/44
[52] U.S. Cl. .............................................................. 514/342
[58] Field of Search ............................................. 514/342

[56] References Cited

U.S. PATENT DOCUMENTS

| | | | |
|---|---|---|---|
| 5,041,455 | 8/1991 | Sauerburg et al. | 514/342 |
| 5,043,345 | 8/1991 | Sauerburg et al. | 514/342 |
| 5,328,923 | 7/1994 | Sauerburg et al. | 514/340 |
| 5,328,924 | 7/1994 | Sauerburg et al. | 514/340 |
| 5,488,056 | 1/1996 | Bodick et al. | 514/305 |
| 5,708,014 | 1/1998 | Bodick et al. | 514/340 |

FOREIGN PATENT DOCUMENTS

| | | | |
|---|---|---|---|
| 0 307 142 A1 | 3/1989 | European Pat. Off. | C07D 417/04 |
| 0 384 288 A2 | 8/1990 | European Pat. Off. | C07D 417/04 |
| 0 709 094 A2 | 5/1996 | European Pat. Off. | A61K 31/44 |
| 0 723 781 A2 | 7/1996 | European Pat. Off. | A61K 31/44 |
| WO 94/20495 | 9/1994 | WIPO | C07D 417/14 |
| WO 94/29303 | 12/1994 | WIPO | C07D 417/04 |
| WO 95/05174 | 2/1995 | WIPO | A61K 31/44 |
| WO 95/17185 | 6/1995 | WIPO | A61K 31/44 |
| WO 96/13168 | 5/1996 | WIPO | A01N 43/90 |

OTHER PUBLICATIONS

Rapaport, et al., *Biol. Psychiatry,* 29, 658–664 (1991).
Katzung, B.G., *Basic & Clinical Pharmacology,* (Appleton & Lange, Norwald), 90–94 (1995).
Sauerburg, et al., *J. Med. Chem.*, 35 2274–2283 (1992).

*Primary Examiner*—Raymond Henley, III
*Attorney, Agent, or Firm*—David M. Stemerick

[57] ABSTRACT

The present invention is directed to a method for using 3-(4-hexyloxy-1,2,5-thiadiazol-3yl)-1,2,5,6-tetrahydro-1-methylpyridine, i.e., xanomeline, for the treatment of autism and mental retardation.

17 Claims, No Drawings

METHOD FOR TREATING MENTAL RETARDATION

This is a 371 of PCT/US97/13184 filed Jul. 28, 1997.

This invention provides a method for using 3-(4-hexyloxy-1,2,5-thiadiazol-3-yl)-1,2,5,6-tetrahydro-1-methylpyridine, (hereinafter referred as "xanomeline"), for the treatment of autism and mental retardation.

Autism and mental retardation are seriously incapacitating conditions for which there has been little available treatment. The patient suffering from autism has gross and sustained impaired reciprocal social interaction. Impairment in communication is marked and sustained as well. The autistic patient suffers from restricted repetitive and stereotyped patterns of behavior, interests, and activies which are non-functional and/or abnormal in either intensity or focus. Further, the juvenile patient younger than three years old displays delays in at least one of the following areas: social interaction, language as used in social communication, or symbolic or imaginative play.

The patient suffering from mental retardation has subaverage general intellectual functioning. The onset of such subaverage intellectual functioning is before the age of 18 (eighteen) years.

Both mental retardation and autism can be debilitating conditions which may require institutionalization, if severe.

Applicants have discovered that 3-(4-hexyloxy-1,2,5-thiadiazol-3-yl)-1,2,5,6-tetrahydro-1-methylpyridine, thought to be a muscarinic agonist, can be useful for treating autism and/or mental retardation. More specifically, the invention provides a method of treating mental retardation in a mammal using 3-(4-hexyloxy-1,2,5-thiadiazol-3-yl)-1,2,5,6-tetrahydro-1-methylpyridine. Further, the present invention provides a method of treating autism in a human using 3-(4-hexyloxy-1,2,5-thiadiazol-3-yl)-1,2,5,6-tetrahydro-1-methylpyridine.

As noted hereinbefore, the compound employed in the method of the present invention is known. Methods of preparing the compound, as well as pharmaceutical formulations containing the compound, are taught by Suaerberg in U.S. Pat. No. 5,043,345 (hereinafter referred to as the "'345 patent") herein incorporated by reference. The '345 patent teaches that xanomeline can be useful for treating Alzheimer's Disease and as a stimulant of the cognitive function of the forebrain and hippocampus of mammals. Unlike Alzheimer's Disease, the onset of mental retardation is before the age of eighteen and has many different etiologies. Further, a patient suffering from autistic disorder may have average or above average intelligence in one or more skills. The autistic patient suffers from a markedly abnormal or impaired development in social interaction and communication and a markedly restricted repertoire of activity and interests. Applicants have discovered that xanomeline can be useful for the treatment of both mental retardation and/or autism. Xanomeline may address the long felt need for treatments which provide a favorable safety profile and effectively provides relief for the patient or individual suffering from autism and/or mental retardation.

The presently claimed invention provides a method for treating autistic disorder, comprising administering an effective amount of a compound of Formula I:

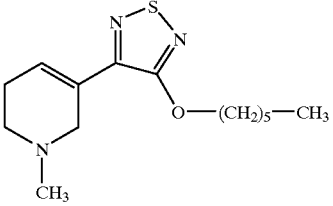

or
a pharmaceutically acceptable salt or solvate thereof to a patient in need of such treatment.

The presently claimed invention provides a method for treating mental retardation, comprising administering an effective amount of a compound of Formula I:

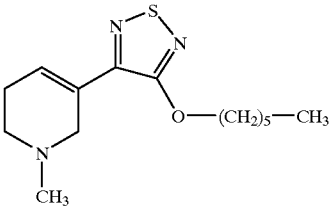

or
a pharmaceutically acceptable salt or solvate thereof to a patient in need of such treatment.

As used herein, the term "autistic disorder" shall refer to a condition characterized as an Autistic Disorder, in the DSM-IV-R. *Diagnostic and Statistical Manual of Mental Disorders, Revised,* 4th Ed. (1994) as catagory 299.00. The DSM-IV-R was prepared by the Task Force on Nomenclature and Statistics of the American Psychiatric Association, and provides clear descriptions of diagnostic catagories. The skilled artisan will recognize that there are alternative nomenclatures, nosologies, and classification systems for pathologic phylogenical conditions and that these systems evolve with medical scientific progress.

As used herein, the term "mental retardation" shall refer to a condition characterized as a Mental Retardation, in the DSM-IV-R. *Diagnostic and Statistical Manual of Mental Disorders, Revised,* 4th Ed. (1994) as catagories 317, 318.xx, and 319. To further clarify, the present invention contemplates the treatment of mild mental retardation, moderate mental retardation, severe mental retardation, profound mental retardation, and mental retardation severity unspecified. Such mental retardation may be, but is not required to be, associated with chromosomal changes, (for example Down's Syndrome due to trisomy 21), heredity, pregnancy and perinatal problems, and other severe mental disorders.

The term "effective amount", as used herein, represents an amount of compound necessary to prevent or treat mental retardation or autistic disorder in a human susceptible to or suffering from mental retardation or autistic disorder following administration to such human. The active compound is effective over a wide dosage range. For example, dosages per day will normally fall within the range of about 0.005 to about 500 mg/kg of body weight. In the treatment of adult humans, the range of about 0.05 to about 100 mg/kg, in single or divided doses, is preferred. However, it will be understood that the amount of the compound actually administered will be determined by a physician, in the light of the relevant circumstances including the condition to be treated, the choice of compound to be administered, the age, weight, and response of the individual patient, the severity of the patient's symptoms, and the chosen route of administration, and therefore the above dosage ranges are not intended to limit the scope of the invention in any way. While the present compound may be administered orally to humans susceptible to or suffering from mental retardation or autism, the compound is particularly well suited to be administered transdermally. When the compound is delivered transdermally, it is preferred that the effective amount is from about 10 mg to about 100 mg per day delivery of base compound. It is especially preferred that such patch delivers an effective amount for about one to seven days.

The compound may further be delivered by a variety of other pharmaceutically accepted routes including, but in no way limited to parenterally, subcutaneous, intranasal, intramuscular and intravenous routes. Such formulations may be designed to provide delayed or controlled release using formulation techniques which are known in the art.

As used herein, the term "mammal" shall refer to the Mammalia class of higher vertebrates. The term "mammal" includes, but is not limited to, a human. The term "treating" as used herein includes prophylaxis in a subject susceptible to the named condition or amelioration or elimination of the condition once it has been established.

The compounds employed in the invention are not believed to act via the GABA/benzodiazepine, serotonin, or dopamine receptor systems in humans. Rather, the activity of the present compound as a treatment for autism in believed to be based upon modulation of muscarinic cholonergic receptors. However, the mechanism by which the present compounds function is not necessarily the mechanism stated supra., and the present invention is not limited by any mode of operation.

Xanomeline has been studied using accepted pharmacological methods such as oxotremorine-M verses N-methylscopolamine binding studies (Freedman et al. *Br. J. Pharmacology*, 93:437–445 (1988). Xanomeline inhibited the binding of $^3$H-oxotremorine-M with an inhibition costant ($K_i$) of 2 nM. The binding of the nuscarinic m1 antagonist ligand, $^3$H-pirezepine, to m1 receptors in hippocampus and $^3$H-guinuclidinyl benzilate to m2 receptors in brain stem was inhibited with $K_i$ values of 5 and 24 nM, respectively.

Muscarinic agonists stimulate the formation of cAMP up to 10 fold in CHO m4 cells treated with pertussisi toxin and the pharmacology is consistent with the mediation by m4 receptors. Eckols K. *Soc. Neurosci Abstr.*, 21:2040 (1995). In this assay, xanomeline efficaciously and potently stimulated the formation of cAMP. Such studies suggest that xanomeline predominantly activates m1 and m4 receptors.

Xanomeline has a moderate affinity for $5HT_{2C}$ and $5HT_{1D}$ receptor subtypes as indicated by $K_i$ values of 120 and 180 nM respectively.

The clinical benefit of xanomeline for the treatment of autism can be supported by the following examples.

EXAMPLE 1

Human Clinical Trials

The activity of xanomeline for treating or alleviating autism can be demonstrated by human clinical trials. The study was designed as a double-blind, parallel, placebo-controlled multicenter trial. The subjects were radomized into four groups, placebo and 25, 50, and 75 mg tid of test compound. The dosages were administered orally with food. Subjects were observed at four visits to provide baseline measurements. Visits 5–33 served as the treatment phase for the study.

During the visits, subjects and observed for behavioral, social interaction, intellectual, and concentration abilities.

Treatment groups are compared with respect to the number and percent of subjects who ever had the symptom during the double-blind portion of the study (visits 5 through 33), at a severity that was worse than during the baseline visits (1 through 4).

We claim:

1. A method for treating autism comprising administering to a mammal in need of such treatment, an effective amount of a compound of Formula I:

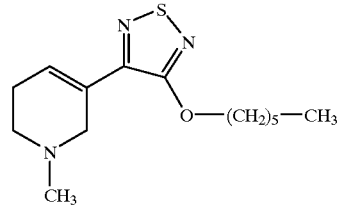

or a pharmaceutically acceptable salt thereof.

2. A method of claim 1 wherein the effective amount is from 1 mg/kg to about 100 mg/kg per day.

3. A method of claim 2 wherein the effective amount is from about 10 mg/kg to about 100 mg/kg per day.

4. A method of claim 1 wherein the effective amount is delivered using a transdermal patch.

5. A method of claim 4 wherein the transdermal patch delivers from about 10 to about 100 mg of base compound per day.

6. A method of claim 5 wherein the transdermal patch delivers an effective amount for one (1) to seven (7) days.

7. A method of claim 1 wherein the mammal is a human.

8. A method for treating mental retardation comprising administering to a mammal in need of such treatment, an effective amount of a compound of Formula I:

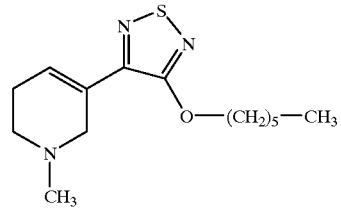

or a pharmaceutically acceptable salt thereof.

9. A method of claim 8 wherein the mammal is a human.

10. A method of claim 9 wherein the effective amount is from 1 mg/kg to about 100 mg/kg per day.

11. A method of claim 10 wherein the effective amount is from about 10 mg/kg to about 100 mg/kg per day.

12. A method of claim 10 wherein the effective amount is delivered using a transdermal patch.

13. A method of claim 12 wherein the transdermal patch delivers from about 10 to about 100 mg of base compound per day.

14. A method of claim 13 wherein the transdermal patch delivers an effective amount for one (1) to seven (7) days.

15. A method of claim 8 wherein the mental retardation is severe mental retardation.

16. A method of claim 8 wherein the mental retardation is moderate mental retardation.

17. A method of claim 8 wherein the mental retardation is mild mental retardation.

* * * * *